US006187913B1

(12) United States Patent
Blumenfeld et al.

(10) Patent No.: US 6,187,913 B1
(45) Date of Patent: Feb. 13, 2001

(54) COVALENTLY CROSSLINKED OLIGONUCLEOTIDES, PREPARATION METHOD AND SYNTHON WHICH IS OF USE IN THE METHOD

(75) Inventors: Marta Blumenfeld; Irena Merenkova, both of Paris (FR)

(73) Assignee: Genset, Paris (FR)

( * ) Notice: Under 35 U.S.C. 154(b), the term of this patent shall be extended for 0 days.

(21) Appl. No.: 08/930,500

(22) PCT Filed: Apr. 2, 1996

(86) PCT No.: PCT/FR96/00493

§ 371 Date: Dec. 23, 1997

§ 102(e) Date: Dec. 23, 1997

(87) PCT Pub. No.: WO96/31523

PCT Pub. Date: Oct. 10, 1996

(30) Foreign Application Priority Data

Apr. 3, 1995 (FR) .................................................. 95 03889

(51) Int. Cl.$^7$ .......................... C07H 21/00; C07C 205/00
(52) U.S. Cl. .................... 536/23.1; 536/25.3; 536/25.32; 501/33; 560/155; 428/402; 546/25; 546/102; 548/304.1; 549/223; 549/227
(58) Field of Search ................................ 536/25.3, 25.32, 536/23.1; 501/33; 560/155; 428/402; 546/25, 102; 548/304.1; 549/223, 227; 552/544; 558/93, 168, 191, 192; 568/933

(56) References Cited

U.S. PATENT DOCUMENTS 5,235,033 * 8/1993 Summerton et al. ................. 528/391
5,414,077 * 5/1995 Lin et al. ............................. 536/24.3
5,451,463 * 9/1995 Nelson et al. ........................ 428/402

FOREIGN PATENT DOCUMENTS

WO88/00201 1/1988 (WO) .
WO92/19732 11/1992 (WO) .
WO93/18052 9/1993 (WO) .

OTHER PUBLICATIONS

Benseler, F. et al, "Synthesis of Suitably–Protected Phosphor–amidites of 2'–Fluoro–2'–Deoxyguanosine and 2'–Amino–2'–Deoxy–guanosine and 2'–Amino–2'Deoxyguanosine for Incorporation Into Oligoribonucleotides", Nucleosides And Nucleotides, vol. 11, No. 7, 1992, pp. 1333–1351.

Kuznetsova, L.G. et al, "Oligodeoxyribonucleotides Containing 2'Amino–2'–Deoxypyrimidine Nucleosides", Bioorg, Khim., vol. 19, No. 4, 1993, pp. 455–466.

* cited by examiner

*Primary Examiner*—James O. Wilson
(74) *Attorney, Agent, or Firm*—Pennie & Edmonds, LLP

(57) ABSTRACT

A double- or single-stranded oligonucleotide comprising one or more respectively inter- or intra-oligonucleotide covalent cross-linkages, wherein the or each covalent linkage consists of an amide bond between a primary amine group of one strand and a carboxyl group of the other strand or the same strand, respectively, said primary amine group being directly substituted in the 2' position of the strand nucleotide monosaccharide ring, and said carboxyl group being carried by an aliphatic spacer group substituted on a nucleotide or nucleotide analog of the other strand or the same strand, respectively. A method for preparing such oligonucleotides, and nucleotide or non-nucleotide synthons useful for preparing an oligonucleotide of the above kind, are also disclosed.

21 Claims, No Drawings

COVALENTLY CROSSLINKED OLIGONUCLEOTIDES, PREPARATION METHOD AND SYNTHON WHICH IS OF USE IN THE METHOD

The present invention relates to covalently crosslinked duplex oligonucleotides, that is to say DNA, RNA or mixed DNA/RNA duplexes the two complementary strands of which are crosslinked covalently.

More specifically, the present invention relates to a single-stranded oligonucleotide possessing intra-oligonucleotide covalent link(s), that is to say a single-stranded oligonucleotide which contains a covalent link between the two sites of the oligonucleotide, or several covalent links between a number, a multiple of two, of sites of the oligonucleotide. In particular, the oligonucleotide can be of the "hairpin" type, that is to say containing two paired fragments of the same strand separated by a non-self-paired loop, the covalent link being located in said paired fragments.

The present invention also relates to a double-stranded oligonucleotide possessing inter-oligonucleotide covalent link(s), that is to say a double-stranded oligonucleotide in which the two paired strands are linked to one another via covalent links between one or more sites of each of said two strands.

Oligonucleotides of this type have been described in Patent Application PCT WO93/18052. They are useful in a therapeutic application, in particular in the so-called "sense" strategy where they are used for their property of hybridizing with factors involved in the transcription of genes involved in pathologies. Sense agents of this type have also been described in Patent Application PCT WO92/19732.

Crosslinked oligonucleotides are also useful as research reagents for purposes of elucidation of the mechanism of DNA-protein interaction. In particular when this interaction is associated with a disturbance of the structure of the double helix (RNA polymerase, methylase, uracylglycosilase and other repair enzymes).

The practical use of crosslinked duplexes enables the level of gene expression in different tissues to be studied in in vitro systems (when specific factors take part in this mechanism), and constitutes an effective means for inhibiting transcription and modulating it.

These duplexes have the especially advantageous property of being more resistant to endonucleases and exonucleases than duplex oligonucleotides without covalent bonding.

An objective of the present invention is to provide oligonucleotides possessing improved covalent crosslinking, that is to say the covalent link must be sufficiently flexible to comply with the helical structure of the duplex or of other secondary and tertiary structures of the DNA.

Another objective of the present invention is to provide a simplified method for preparing these covalently crosslinked oligonucleotides.

A further objective of the present invention is to obtain a covalent link which can be cut without disrupting the hybridization of the covalently linked oligonucleotides or portions of oligonucleotides.

In the document WO93/18052, covalently cross-linked duplexes have been described in which the covalent link results from the reaction of an aldehyde group, more specifically a dialdehyde group, and an amine group. This reaction yields a Schiff's base, followed by a reduction with a borohydride which results in a covalent hydrazide linkage.

A reaction is also described between an aldehyde and hydroxyl groups, which results in an acetal linkage.

The present invention consists in using a covalent link of the amide type

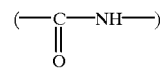

between a primary amine group and a carboxyl group. This type of linkage makes it possible to achieve the objectives set by the present invention.

Although this type of amide link is advantageous since its chemistry is much simpler, a single condensation reaction in the presence of a condensing reagent of the carbodiimide type is necessary, it was not described in the document WO93/18052 for the following reason. This type of amide link, when it involves two nucleic acids, more specifically two oligonucleotides, must be produced in an acid medium at a pH of approximately 6.5. Now, the pKa of an aliphatic primary amine group is of the order of 11. Under the reaction pH conditions of the order of 6.5, the aliphatic primary amine group is hence predominantly in protonated form and the nucleophilic form of the amine is virtually nonexistent, so that the reaction cannot take place or, at all events, does so in very low yield.

However, according to the present invention, advantage has been taken of the fact that an amine group situated at the 2' position of a 2'-deoxynucleotide possesses a markedly lower pKa, namely of the order of 7.4, which permits coupling of this amine with a carboxyl group under pH conditions compatible with the coupling of two oligonucleotides. As a result of the reaction pH level, it is maintained to a greater extent in free, unprotonated form, thus remaining nucleophilic.

An essential feature of the present invention is hence to use a modified nucleotide carrying an $NH_2$ group at the 2' position of a 2'-deoxynucleotide, coupled to another modified nucleotide or modified nucleotide analog carrying an aliphatic group having a carboxyl group at its end.

More specifically, the subject of the present invention is a double-stranded or single-stranded oligonucleotide containing one or more inter- or intra-oligonucleotide covalent crosslink(s), respectively, characterized in that the or each covalent link consists of an amide linkage between a primary amine group of one strand and a carboxyl group of the other strand or of the same strand, respectively, said primary amine group being substituted directly at the 2' position of the saccharide ring of a nucleotide of one strand, and said carboxyl group being carried by an aliphatic spacer group substituted on a nucleotide or a nucleotide analog of the other strand or of the same strand, respectively.

"Nucleotide analog" is understood to mean a non-nucleotide insert which contains, like the natural nucleotides, a linear motif of 3 carbon atoms between the two inter-nucleotide links, so that said motif has as its skeleton:

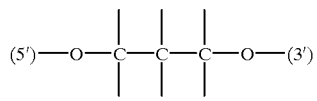

This non-nucleotide insert makes it possible to adhere to the natural inter-nucleotide distance. Said "nucleotide analog" takes the form of a monovalent residue or of a divalent residue if it replaces a terminal nucleotide or a nonterminal nucleotide, respectively, in the oligonucleotide.

The aliphatic group included in the covalent link serves as a spacer group, since its size must be such that the covalent link between the two oligonucleotides in question comprises a linear chain whose skeleton contains from 5 to 25 aligned atoms, so that the distance between the two strands on the one hand and the spatial conformation of the double helix on the other hand are adhered to and permit good hybridization between the two strands.

In one embodiment, said carboxyl group is carried by a nucleotide analog consisting of a non-nucleotide insert of the 1,3-propanediol type substituted at the 2 position with an aliphatic group (R) carrying said carboxyl group at its end.

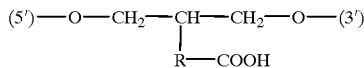

In an other embodiment, said carboxyl group is carried by an aliphatic group substituted at the 2' position of a 2'-deoxynucleotide.

However, it is preferable to use a nucleotide analog, since the reactions are easier to carry out inasmuch as there is no need to protect the nucleotide in the various other functional groups of the saccharide ring and/or of the purine or pyrimidine base.

The nucleotide(s) and nucleotide analog, where appropriate, involved in an inter- or intramolecular covalent link can be in a pairing position, that is to say face to face on each strand of the paired fragments.

However, depending on the size of said aliphatic group, it can be preferable in some cases for the nucleotide(s) and nucleotide analog involved in a covalent link not to be in a pairing position, and to be offset by one or more nucleotides relative to the pairing position. Thus, suitably, the nucleotide(s) and nucleotide analog involved in a covalent link are offset by 1 to 5 nucleotides relative to the pairing position.

Advantageously, said aliphatic group contains a linear chain of 3 to 23 aligned atoms between said amide linkage and the site of the nucleotide or nucleotide analog on which it is substituted, which corresponds to a distance of 5 to 25 atoms between the nucleotide(s) and/or nucleotide analog involved in the link, as mentioned above.

As a further preference, said aliphatic group contains from 7 to 16 atoms.

In one embodiment, said aliphatic group contains 9 atoms, and the nucleotide and nucleotide analog involved in the covalent link are offset by 2 nucleotides relative to the pairing position.

Said aliphatic spacer group substituted with a carboxyl group can itself result from the acylation with an acid anhydride

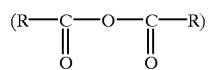

of a primary amine group substituted directly at the 2' position of a nucleotide or at the 2 position of a nucleotide analog.

In an advantageous variant, said aliphatic spacer group substituted with a carboxyl group results from the acylation of an amine group substituted directly at the 2' position on a nucleotide or on a nucleotide analog at the 2 position with an amino acid whose $NH_2$ end is itself acylated with an acid anhydride.

The example in which the amino acid is β-alanine may be mentioned in particular.

Suitably, the acid anhydride is a cyclic anhydride such as succinimic acid anhydride or tartaric anhydride.

In the case where the covalent link contains a β-alanine coupled to a succinimic or tartaric anhydride, a residue at the 2' position of a 2'-deoxynucleotide of one strand is linked to the residue at the 2 position of an analog of the 1,3-propanediol type of another strand or of the same strand via a divalent residue of formula

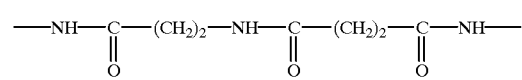

or

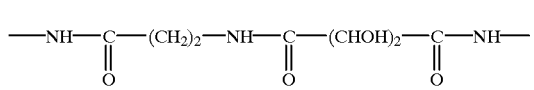

respectively.

Advantageously, the acid anhydride contains a cis-glycol group. In effect, this glycol group can be cleaved in mild oxidation reactions without disrupting the hybridization of the duplex.

Another advantage of the amine groups at the 2' position of a 2'-deoxynucleotide or at the 2 position of a nucleotide analog, in particular of the 1,3-propanediol type, is the possibility of obtaining synthons which can be employed in conventional methods of oligonucleotide synthesis with the $NH_2$ group at the 2' position protected, in particular, by a trifluoroacetyl group

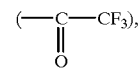

in particular in automatic phosphoramidite synthesis reactions.

Thus, one or more modification(s) can be introduced into an oligonucleotide directly in the course of synthesis in any predetermined site of the oligonucleotide chain using a suitable monomeric synthon.

Hence the subject of the present invention is also a nucleotide synthon which is of use in the preparation of an oligonucleotide according to the present invention, characterized in that it contains the 5' and 3' ends suitably protected in order for it to be used in a method of automatic or manual synthesis of nucleic acids and an amine group substituted at the 2' position protected by a trifluoroacetyl group.

This trifluoroacetyl group can then be selectively removed for the purpose of coupling the oligonucleotide containing it with an acid anhydride.

The subject of the present invention is, in addition, a non-nucleotide synthon which is of use in the preparation of an oligonucleotide according to the present invention, characterized in that it consists of a propanediol compound the hydroxyl functions of which at the 1 and 3 positions are protected by the conventional protective groups for the 5' and 3' functions of nucleotides in oligonucleotide synthesis reactions, and the 2 position of which is substituted directly with an $NH_2$ group or an amino acid acyl residue whose free $NH_2$ group is protected by a trifluoroacetyl group.

Said hydroxyl groups are protected by protective groups used in the phosphoramidite methods of oligonucleotide synthesis.

In an embodiment which is of use for a phosphoramidite synthesis, the nucleotide synthon corresponds to the formula:

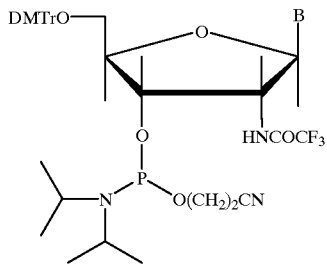

In one embodiment, the non-nucleotide synthon corresponds to the formula:

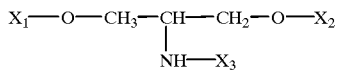

in which $X_1$ and $X_2$ are conventional protective groups for the 5'- and 3'-OH groups of a nucleotide, used in the methods of oligonucleotide synthesis. $X_3$ is an amine group-protecting group or an amino acid acyl residue whose $NH_2$ group is protected by an amine group-protecting group.

In particular, a synthon of the following formula is used:

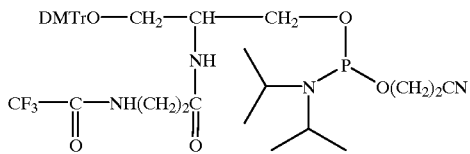

Lastly, the subject of the present invention is a method for preparing an oligonucleotide according to the invention, characterized in that a covalent link of the amide type is produced between a primary amine group of one strand and a carboxyl group of the other strand or of another portion of the same strand, by a condensation reaction at pH 6.5 in the presence of a condensing agent.

Suitably, the condensing agent is water-soluble carbodiimide.

Advantageously, the strand containing a carboxyl group is prepared from a strand containing an amine group, obtained using conventional nucleotide synthons and a synthon according to one of claims 15 to 20, which is coupled to an acid anhydride containing a said aliphatic group.

The principle of the chemical synthesis of nucleic acids on a solid support is nowadays widely described in the specialized literature, and a number of apparatuses are available on the market which perform all or part of the steps of the synthesis automatically. Among the chemical methods described, the so-called phosphoramidite method (EP 0 035 719 B1, EP 617-46) displays at the present time sufficient efficacy for the production of nucleic acids on an industrial scale.

Other features and advantages of the present invention will become apparent in the light of the detailed description which follows.

Oligonucleotides (A) (SEQ ID NO:1) and (B) (SEQ ID NO:2) were prepared according to the standard procedure of phosphoramidite oligonucleotide synthesis.

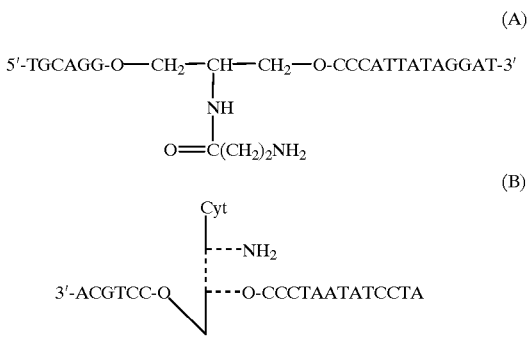

The coupling of (A) (SEQ ID NO:1) with succinimic anhydride was then carried out to obtain (C) (SEQ ID NO:1):

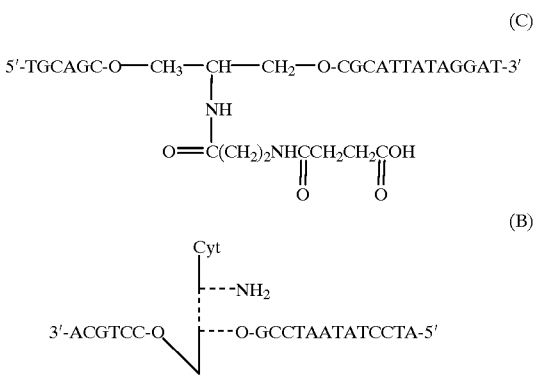

The coupling of the two strands (B) and (C) was then carried out to obtain the following duplex:

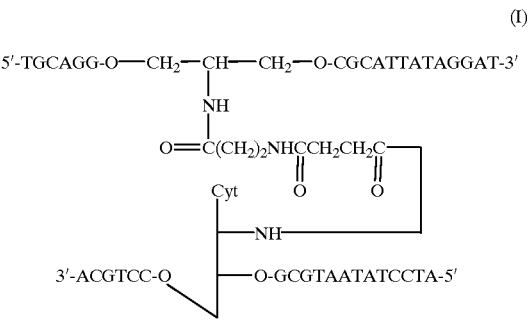

For this purpose, the 3'-phosphoramidite 2'-amino-2'-deoxycytidine (2) and 2'-amino-2'-deoxyuridine (1) nucleotides on the one hand and the phosphoramidite of the non-nucleotide insert on the other hand were synthesized.

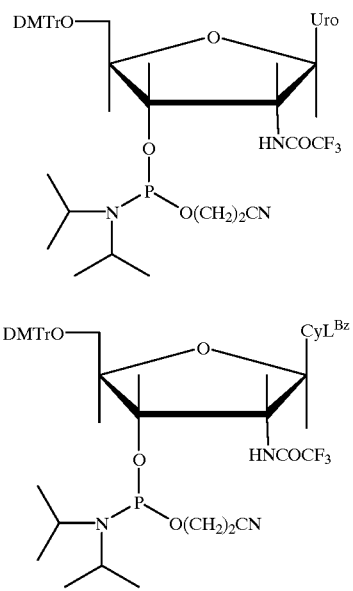

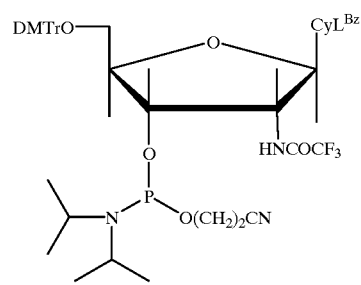

An initial aliphatic amine group located on a non-nucleoside insert (3) was introduced into the second strand of the target duplex. The corresponding phosphoramidite (4) was synthesized from an active ester of β-alanine blocked with N-Fmoc (5) and the dimethoxytrityl (Dmtr) derivative of 2-amino-1,3-propanediol (6) (Scheme 1), proceeding as follows:

condensation of the compounds (5) and (6) in dioxane to produce the target compound (3);

phosphitylation of the compound (3) with β-cyanoethyl N,N-diisopropylamidochlorophosphite to form the phosphoramidite synthon (4).

The synthesis of the p-nitrophenyl ester of β-alanine blocked with N-FMOC (5) is given in Scheme 2, and was carried out according to the following steps:

blocking of the amine group of β-alanine (7) using Fmoc protection by reaction with Fmoc-succinimide (8), obtaining of the activated ester of β-alanine blocked with N-Fmoc (5) by the action of p-nitrophenol on (9) using dicyclohexylcarbodiimide present in dioxane.

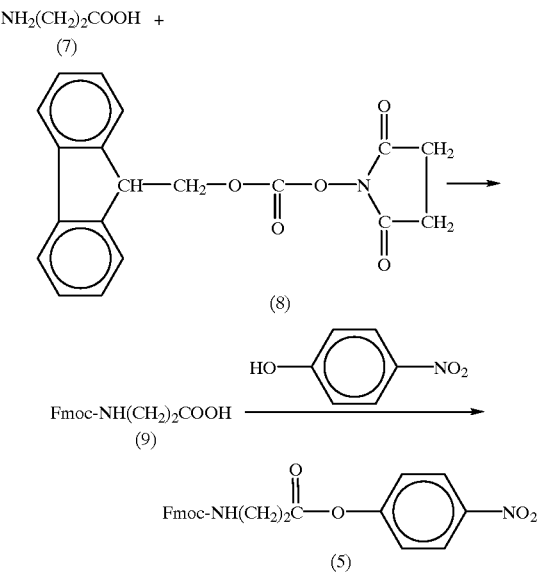

The preparation of 1-O-dimethoxytrityl-2-amino-propanediol (6) is depicted in Scheme 3 and involved the following reactions:

blocking of the primary amine function of 2-amino-1,3-propanediol (10) using the trifluoroacetyl group,

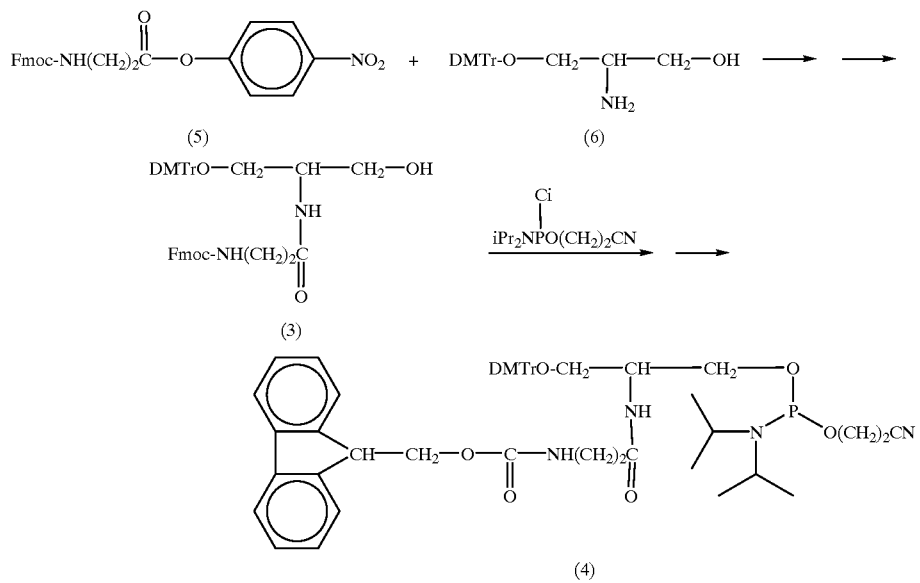

protection of each of the two hydroxyl groups of the compound (11) by the action of dimethoxytrityl chloride in pyridine (1 mol per 0.5 mol of compound (11)). removal of the protection by trifluoroacetyl by the action of concentrated ammonium hydroxide solution.

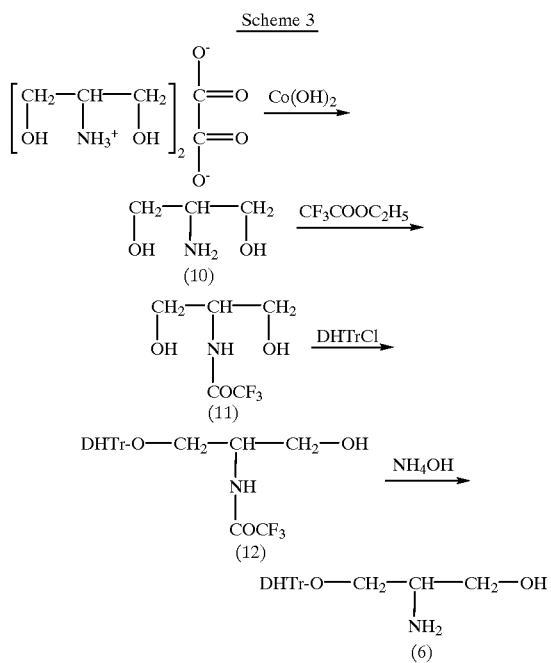

Scheme 3

The target compound (4), containing the aliphatic amine group, was introduced directionally at a precisely defined site of an oligonucleotide chain in a standard so-called phosphoramidite procedure of oligonucleotide synthesis. This non-nucleoside analog maintains the distance of 3 carbon atoms (characteristic of natural nucleosides) between the hydroxyls forming the inter-nucleotide link. Using the compound (4), numerous modified oligonucleotides were obtained. It is nevertheless preferable to use a trifluoroacetyl protective group, since TFA is easier to remove selectively than the Fmoc group. The aliphatic primary amine group thus inserted into the modified oligonucleotides proved to be highly reactive in reactions having electrophilic reagents. Thus, a reaction was carried out with acetic anhydride followed by ion-pair HPLC analysis of the products of the reaction, as well as the reaction with fluorescein isothiocyanate (FITC) followed by spectrophotometric analysis of the products. The spectrum of the product resulting from the reaction with FITC exhibited two absorption peaks at 260 and at 495 nm (ratio 6:1) corresponding to the oligonucleotide and fluorescein, respectively.

Furthermore, the carboxyl group was introduced into the modified oligonucleotides containing the amine function, by the condensation reaction on (4) with succinimic anhydride. The reaction yield of products resulting from the carboxylation of the oligonucleotides with succinimic anhydride was greater than 95%.

It should be noted that the retention time of the modified oligonucleotides analyzed by ion-pair HPLC varied with the nature of the functional groups introduced. Thus, the retention time of the oligonucleotides possessing the amine group was lower than that of the natural oligonucleotides possessing an analogous primary structure. This was due to the fact that such oligonucleotides had an additional positive charge. The retention time of the oligonucleotides possessing the carboxyl group was, on the contrary, higher as the result of an additional negative charge.

The amine function located on the non-nucleoside insert of the oligonucleotide was also acylated with tartaric anhydride. The crosslinked duplex synthesized using such a precursor containing a carboxyl possesses a cis-glycol type link. In this crosslinked duplex, it is possible to separate the chains of the duplex (cleaved the link between the chains) by an oxidation reaction.

The examples which follow illustrate the present invention.

EXAMPLE 1

Standard Synthesis of Oligonucleotides

Oligonucleotide syntheses were carried out on an Applied Biosystems 380B synthesizer according to the standard phosphoramidite protocols and cycles using reagents supplied by the manufacturer. When modified phosphoramidites were used, a longer coupling time (5 to 7 min) was used. The oligonucleotides were normally synthesized on a scale of 0.4 μmol in the "Trytil-On" mode. The standard conditions of deprotection (30% ammonium, 55° C., 16 h) were used.

HPLC was carried out on an Altex equipped with a Kratos UV detector. The oligonucleotides were analyzed and purified by reversed-phase high pressure liquid chromatography on a Diasorb 130 $C16_T$ (7 micron) column (4 mm ID×250 mm). The solvent A was 0.1 M $AcONH_4$ (ammonium acetate), pH 7.0, the solvent B was 0.1 M $AcONH_4$, pH 7.0, 40% (V/V) acetonitrile. The linear gradient from 0% to 100% of B was applied over 60 min. The eluate was monitored at 260 nm or at 290 nm.

For the result of the reaction analysis, an ion-pair HPLC was used with the step of 2 residues per min. A Waters HPLC gradient system, a 4×250 mm column packed with Diasorb 130 $C16_T$ (7 micron), an eluant comprising 50 mM K phosphate (pH 7.0) with 2 mM tetrabutylammonium and an acetonitrile gradient from 5 to 40%, a flow rate of 1 ml/min and a temperature of 45° C. were used.

All the oligonucleotide sequences are depicted in the list in a standard 5' to 3' order from left to right. The prefix "d" (deoxy) is omitted in the identification of the 2'-deoxyribonucleosides and the oligodeoxyribonucleotides.

EXAMPLE 2

Preparation of activated and protected nucleotides and of non-nucleoside inserts having a spacer group and an active function group.

Thin-layer chromatography (TLC) was carried out on Silica gel 60 $F_{254}$ plates (Merck), column chromatography was carried out on Silica gel 60 (Merck) using one of the following solvent systems a) $CHCl_3$/EtOH 95:5 (v/v); b) $CHCl_3$/EtOH 9:1 (v/v); c) $CH_2Cl_2$/$CH_3OH$/$Et_3N$ 94:5:1 (v/v/v), and UV spectra were obtained on a 150-20 spectrophotometer (Hitachi, Japan).

5'-0- (4,4'-Dimethoxytrityl)-2'-trifluoroacetamido-2'-deoxyuridine 3'-0- (β-cyanoethyl-N,N-diisopropylamido) phosphite (1) and 5'-0-(4,4'-dimethoxytrityl)-$N^4$-benzoyl-2'-trifluoroacetamido-2'-deoxycytidine 3'-0-(β-cyanoethyl-N,N-diisopropylamido)phosphite (2) were prepared according to Kuznetsova L. G., Romanova E. A., Volkov E. M., Tashlitsky V. N., Oretskaya T. S., Krynetskaya N. F., Shabarova Z. A. Bioorganicheskaya khimia (Russ.) 1993, 19, 455–466.

Preparation of 2-amino-1,3-propanediol (10). 2-Amino-1,3-propanediol oxalate (3.0 g, 11 mmol) was dissolved in 100 ml of water. Calcium hydroxide (0.82 g, 11 mmol) was added with stirring. After 30 min, the precipitate was filtered off and the supernatant was concentrated under vacuum. 1.9 g (95%) are obtained.

The trifluoroacetylation of (10) was carried out according to the method described in Kuznetsova L. G., Romanova E. A., Volkov E. M., Tashlitsky V. N., Oretskaya T. S., Krynetskaya N. F., Shabarova Z. A. Bioorganicheskaya khimia (Russ.) 1993, 19, 455–466.

The tritylation of 2-trifluoroacetamido-1,3-propanediol (11) was carried out using the similar procedure intended for nucleotides: Jones R. A., Oligonucleotide synthesis: a Practical Approach. Ed. by M. J. Gait, Oxford, Washington D.C.: IRL Press, 1984, 23–24.

Preparation of 1-dimethoxytrityl-2-amino-3-propanol (6). The compound (12) (2.94 g, 6 mmol) was dissolved in 30 ml of EtOH, and $NH_4OH$ (18 ml) was added dropwise with stirring. The reaction mixture was heated to 45° C. for 2 hours and the solvents were removed under vacuum. The residue was purified on a column of silica gel eluted with the solvent system b) to give 1.73 g (73%) (6); $R_f$ 0.25 (system a).

Preparation of N-fluorenylmethoxycarbonyl-β-alanine (9). 9-Fluorenylmethoxysuccinimide (8) (0.86 g, 2.56 mmol) was added dropwise with stirring to a solution of β-alanine (7) (0.46 g, 5.16 mmol) in 10 ml of water with the aid of 700 ml of $Et_3N$. After 30 min, the mixture was concentrated under vacuum and the residue was added to 8 ml of 1.5 M HCl. The insoluble matter was removed by filtration, washed twice with water and dried at 45° C. Production of (9) 0.76 g (95%), $R_f$ 0.5 (system a).

Preparation of N-fluorenylmethoxycarbonyl-β-alanine p-nitrophenyl ether (5). p-Nitrophenol (0.40 g, 3.2 mmol) was added to (9) (0.90 g, 2.9 mmol) dissolved in 5 ml of dehydrated dioxane. The mixture was stirred for 24 h at room temperature. The insoluble matter was removed by filtration. The filtrate was concentrated to dryness under vacuum. Production of (5) 1.2 g (95%). $R_f$ 0.8 (system a).

The compound (3) was prepared from (5) (1.2 g, 2.8 mmol) by reaction with (6) (1.14 g, 0.3 mmol) in dehydrated dioxane (10 ml). The mixture was stirred for 24 h at room temperature. The solvent was removed under reduced pressure, and the residue was purified on a column of silica gel with the solvent system c). 1.2 g of (3) (63%) is obtained. $R_f$ 0.4 (system b).

$^1$H NMR ($CDCl_3$) 6.1 (d, 1H, CH—N$\underline{H}$—CO, J 7.9 Hz); 5.53 (t, 1H, $CH_2$—N$\underline{H}$—CO, J 6.1 Hz); 4.35 (d, 2H, O—C$\underline{H}_2$—CH, J. 7.0 Hz); 4.18 (t, 1H, $CH_2$—C$\underline{H}$, J 7.0 Hz); 4.1 (m, 1H, $CH_2$—C$\underline{H}$—$CH_2$), 3.75 (s, 6H, C$\underline{H}_3$O); 3.7 (2d, 2H, OC$\underline{H}_2$—CH, $J_1$ 11.3 Hz, $J_2$ 4.8 Hz); 3.48 (m, 2H, $CH_2$—C$\underline{H}_2$—NH); 3.3 (2d, 2H, CH—C$\underline{H}_2$OH, J 11.3 Hz, J 4.0 Hz), 2.41 (m, 2H, CO—C$\underline{H}_2$—$CH_2$).

The phosphitylation of (3) was carried out according to Jones R. A., Oligonucleotide synthesis: a Practical Approach. Ed. by M. J. Gait, Oxford, Washington D.C.: IRL Press. 1984.

EXAMPLE 3

Preparation of oligonucleotides having 2'-amino-2'-deoxypyrimidine nucleosides

1. Oligonucleotide containing a single 2'-amino-2-deoxycytidine residue

The oligonucleotide of sequence oligomer (A) (SEQ ID NO:3)

ATC CTA TAA TGC GC$^n$C CTG CA in which C$^n$ represents a 2'-amino-2'-deoxycytidine nucleotide, was prepared using the procedure of Example 1. The 2'-amino-2'-deoxycytidine situated in the middle of the sequence was added during the synthesis using the 2'-amino-2'-deoxycytidine phosphoramidite (2).

2. Oligonucleotides containing a single 2'-amino-2'-deoxyuridine residue

The oligonucleotides of sequence

Oligomer (B)   G CCA CTC GGA AAG TCC CCT CU$^n$A CCG
(SEQ ID NO:4)

Oligomer (C)   G CCA U$^n$TC GGA AAG TCC CCT CTA CCG
(SEQ ID NO:5)

Oligomer (D)   G CCA CTC GGA AAG TGA GCT CU$^n$A CCG
(SEQ ID NO:6)

Oligomer (E)   G CCA U$^n$TC GGA AAG TGA GCT CTA CCG
(SEQ ID NO:7)

in which U$^n$ represents a 2'-amino-2'-deoxyuridine nucleotide, were prepared using the procedure of Example 1. The 2'-amino-2'-deoxyuridine situated in the middle of the sequence was added during the synthesis using the 2'-amino-2'-deoxyuridine phosphoramidite (1).

3. Oligonucleotides containing multiple residues of 2'-amino-2'-deoxyuridine

The oligonucleotides of sequence

Oligomer (F)   G CCA U$_n$TC GGA AAG TCC CCT CU$_n$A CCG
(SEQ ID NO:8)

Oligomer (G)   G CCA U$_n$TC GGA AAG TGA CGT CU$_n$A CCG
(SEQ ID NO:9)

in which U$^n$ represents a 2'-amino-2'-deoxyuridine, were prepared using the procedure of Example 3.2.

EXAMPLE 4

Preparation of oligonucleotides having a non-nucleoside insertion

1. Oligonucleotides containing a single non-nucleoside insertion

The oligonucleotides of sequence

Oligomer (H)   TCG AGG NGC GCA TTA TAG GAT
(SEQ ID NO:10)

Oligomer (I)   CGG TNG AGG GGA CTT TCC GAG TGG C
(SEQ ID NO:11)

Oligomer (J)   CGG TAG AGG GGA CTT TCC GAN TGG C
(SEQ ID NO:12)

Oligomer (K)   CGG TNG AGC TCA CTT TCC GAG TGG C
(SEQ ID NO:13)

Oligomer (L)   CGG TAG AGC TCA CTT TCC GAN TGG C
(SEQ ID NO:14)

Oligomer (M)   CGG TAG NGG GGA CTT TCC GAG TCC C
(SEQ ID NO:15)

in which N represents a non-nucleoside insert, were prepared using the procedure of Example 1. The non-nucleoside insert was introduced into the sequence during the synthesis using a non-nucleoside phosphoramidite (4). The oligonucleotides were prepared using a standard phosphoramidite procedure. They were deprotected by the normal deprotection procedure, purified by HPLC and detritylated.

2. oligonucleotides containing multiple non-nucleoside insertions

The oligonucleotides of sequence

```
Oligomer (N)    CGG TNG AGG GGA CTT TCC GAN TGG C
(SEQ ID NO:16)

Oligomer (O)    CGG TNG AGC TCA CTT TCC GAN TGG C
(SEQ ID NO:17)
``` in which N represents a non-nucleoside insert, were prepared using the procedure of Example 4.1.

3. The carboxylation of the amine group located on the non-nucleoside insert of the oligomers (H) to (O) was carried out with succinimic anhydride in 0.25 M sodium bicarbonate buffer (pH 8). 1.0 $A_{260}$ unit of oligonucleotide containing amines was dissolved after removal of the salts in the 500 ml of 0.25 M sodium bicarbonate buffer (pH 8), and 500 ml of 0.1 M succinic anhydride in anhydrous acetonitrile were added. The mixture was stirred for 3 h at 37° C. The reaction mixture was isolated by a gel filtration method using a Sephadex G-25 column. The final product was analyzed using reversed-phase HPLC in an ion-pair mode. A Waters HPLC gradient system, a 4×250 mm column packed with Diasorb 130 $G16_T$ (7 micron), an eluant comprising 50 mM K phosphate (pH 7.0) with 2 mm tetrabutylammonium and an acetonitrile gradient from 5 to 40%, a flow rate of 1 ml/min and a 45° C. temperature were used. This will result in oligonucleotides (H') to (O') having a carboxyl function located on a non-nucleoside insert, the use of which is possible in crosslinking reactions.

EXAMPLE 5

Coupling reaction of oligonucleotides having a 2'-amine function of a 2'-deoxynucleoside with oligonucleotides having a carboxyl group located on a non-nucleoside insert in a complementary duplex.

A. Oligonucleotides forming a double-stranded duplex having a covalent link between the two strands. The modifications in the oligonucleotide duplexes are opposite one another.

The crosslinked duplex I

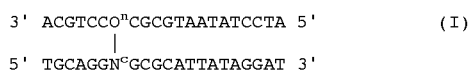

in which $N^c$ represents a non-nucleoside insert having a carboxyl group and "|" represents the crosslink between the carboxyl and amine functions of the oligonucleotide strands is prepared by a reaction carried out in 0.05 M MES buffer (pH 6.7) with 0.02 M $MgCl_2$. 0.1 $A_{260}$ unit of the two oligomers (A) and (H') were dissolved in 37.5 ml of buffer, the mixture was heated to 95° C. and then cooled slowly, and 37.5 ml of 0.4 M CDI (carbodiimide) in the same buffer were added. After 120 h, the reaction mixture was analyzed and the final product was isolated using a reversed-phase HPLC in an ion-pair mode as described above.

The production of the crosslinked duplex (I) was obtained in a 26% yield.

According to a similar procedure, crosslinked duplexes were prepared with productions ranging from 56% to 82%.

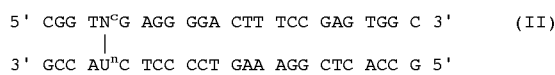

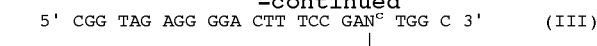
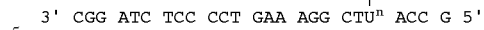

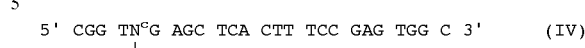

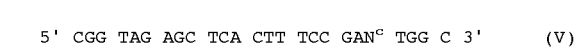
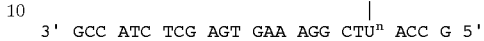

B. Oligonucleotides forming a double-stranded duplex having two covalent links between the chains. The modifications in the oligonucleotide duplexes are opposite one another.

The crosslinked duplexes

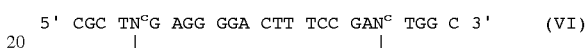
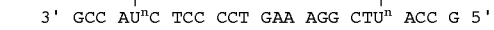

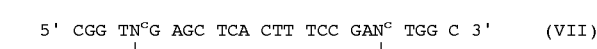
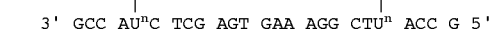

in which $N^c$ represents a non-nucleoside insert having a carboxyl group and "|" represents the crosslink between the carboxyl and amine functions of the oligonucleotide strands are prepared in a similar manner to Example 5.A. The productions of the duplexes (VI) and (VII) are 57% and 84%, respectively.

It is possible to demonstrate the presence of a crosslinked duplex with two covalent links using the restriction endoculease Alu I, which recognizes the double-stranded sequence 5'. . . AGCT . . .3'. As control, we use the crosslinked duplexes (II) and (III) possessing a crosslink.

C. Oligonucleotides forming a double-stranded duplex having a covalent link between the chains. The modification in one of the oligonucleotides of the duplex is offset relative to the other one of two nucleotides.

duplex I possessing offset crosslink

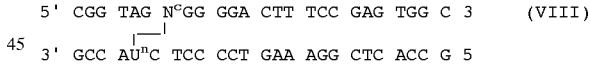
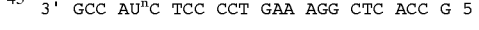

The production of (VIII) is 84%.

EXAMPLE 6

Stability of the duplexes

The thermal melting curves were determined using a 150-20 spectrophotometer (Hitachi, Japan). To determine the $T_m$ values, the first derivative was calculated. The melting behavior of the crosslinked duplexes was determined in 0.05 M MES buffer (pH 6.5, 0.02 M $MgCl_2$). For purposes of comparison, the thermal stability of natural duplexes of analogous structure and of duplexes composed of modified oligonucleotide precursors was studied.

| Duplex number | Duplex type | $T_m$, ° C. |
|---|---|---|
| I | natural | 63 |
|   | unlinked | 34 |
|   | crosslinked | 68 |

-continued

| Duplex number | Duplex type | $T_m$, °C. |
|---|---|---|
| II | natural | 77 |
|  | unlinked | 74 |
|  | crosslinked | 85 |
| VIII | natural | 77 |
|  | unlinked | 74 |
|  | crosslinked | 86 |

The higher $T_m$ of the crosslinked duplexes confirmed the stabilization resulting from the presence of the covalent link between the two strands.

EXAMPLE 6

Resistance of the crosslinked duplexes to specific exonucleases.

The stability of the compound to hydrolysis resulting from the action of a mixture of a snail slime phosphodiesterase and an alkaline phosphatase was studied under strict conditions of complete enzymatic hydrolysis (56° C., 180 min) followed by a reversed-phase HPLC of the hydrolysate. Under these conditions, the natural duplex and the mixture of modified oligonucleotide precursors (oligomers (A) and (H)) were hydrolyzed completely, whereas the "linked" duplex (I) was only 30% hydrolyzed. This small hydrolysis is undoubtedly a result of the covalent link present between the oligonucleotides constituting the "linked" duplex (I).

What is claimed is:

1. Double-stranded or single-stranded oligonucleotide containing one or more inter- or intra-oligonucleotide covalent crosslink, respectively, characterized in that the or each covalent crosslink consists of an amide linkage between a primary amine group of one strand and a carboxyl group of the other strand or of the same strand, respectively, said primary amine group being substituted directly at the 2' position of the saccharide ring of a nucleotide of one strand, and said carboxyl group being carried by an aliphatic spacer group substituted on a nucleotide or a non-nucleotide insert of the other strand or of the same strand, respectively.

2. Oligonucleotide according to claim 1, characterized in that said carboxyl group is carried by a non-nucleotide insert consisting of 1,3-propanediol substituted at the 2 position with an aliphatic group carrying said carboxyl group at its end.

3. Oligonucleotide according to claim 1, characterized in that said carboxyl group is carried by an aliphatic group substituted at the 2' position of a 2'-deoxynucleotide.

4. Oligonucleotide according to claim 1, characterized in that the nucleotide(s) and non-nucleotide insert involved in an inter- or intramolecular covalent link are in a pairing position.

5. Oligonucleotide according to claim 1, characterized in that the nucleotide(s) and non-nucleotide insert involved in a covalent link are not in a pairing position.

6. Oligonucleotide according to claim 5, characterized in that the nucleotide(s) and non-nucleotide insert involved in a covalent link are offset by 1 to 5 nucleotides relative to the pairing position.

7. Oligonucleotide according to claim 1, characterized in that said aliphatic group contains a linear chain of 3 to 23 atoms between said amide linkage and the site of the nucleotide or non-nucleotide insert on which it is substituted.

8. Oligonucleotide according to claim 7, characterized in that said aliphatic group contains from 7 to 16 atoms.

9. Oligonucleotide according to claim 8, characterized in that said aliphatic group contains 9 atoms, and the nucleotide and non-nucleotide insert involved in the covalent link are offset by 2 nucleotides relative to the pairing position.

10. Oligonucleotide according to claim 1, characterized in that said aliphatic spacer group substituted with a carboxyl group results from the acylation with an acid anhydride of a primary amine group substituted directly at the 2' position of a nucleotide or at the 2 position of a non-nucleotide insert.

11. Oligonucleotide according to claim 1, characterized in that said aliphatic spacer group substituted with a carboxyl group results from the acylation of an amine group substituted directly at the 2' position on a nucleotide or on a non-nucleotide insert at the 2 position with an amino acid whose $NH_2$ end is itself acylated with an acid anhydride.

12. Oligonucleotide according to claim 11, characterized in that the amino acid is β-alanine.

13. Oligonucleotide according to claim 10, characterized in that the acid anhydride is a cyclic anhydride such as succinimic anhydride or tartaric anhydride.

14. Oligonucleotide according to claim 1, characterized in that a monovalent residue at the 2' position of a 2'-deoxynucleotide of one strand is linked to the monovalent residue at the 2 position of an analog of the 1,3-propanediol type of another strand or of the same strand via a divalent residue of formula $$-\text{NH}-\underset{\underset{O}{\|}}{C}-(CH_2)_2-\text{NH}-\underset{\underset{O}{\|}}{C}-(CH_2)_2-\underset{\underset{O}{\|}}{C}-\text{NH}- \text{ or}$$

$$-\text{NH}-\underset{\underset{O}{\|}}{C}-(CH_2)_2-\text{NH}-\underset{\underset{O}{\|}}{C}-(CHOH)_2-\underset{\underset{O}{\|}}{C}-\text{NH}-.$$

15. Non-nucleotide synthon which is of use in the preparation of an oligonucleotide according to claim 1, characterized in that it consists of a propanediol compound the hydroxyl functions of which at the 1 and 3 positions are protected by the conventional protective groups for the 5' and 3' functions of nucleotides in oligonucleotide synthesis reactions, and the 2 position of which is substituted directly with an $NH_2$ group or an amino acid acyl residue whose free $NH_2$ group is protected by a trifluoroacetyl group.

16. Non-nucleotide synthon according to claim 15, characterized in that it corresponds to the formula $$X_1-O-CH_2-\underset{\underset{NH-X_3}{|}}{CH}-CH_2-O-X_2$$

where $X_1$ and $X_2$ are conventional protective groups for the 5'- and 3'-OH groups of a nucleotide, used in the methods of oligonucleotide synthesis. $X_3$ is an amine group-protecting group or an amino acid acyl residue whose $NH_2$ group is protected by an amine group-protecting group.

17. Non-nucleotide synthon according to claim 16, characterized in that it corresponds to the formula $$\text{DHTrO}-CH_2-\underset{\underset{\underset{\underset{O}{\|}}{CF_3-C-NH(CH_2)_2C}}{\underset{\underset{O}{\|}}{NH}}}{CH}-CH_2-O-P\begin{pmatrix}N\begin{pmatrix}\\\\\end{pmatrix}\\O(CH_2)_2CN\end{pmatrix}.$$

18. Method for preparing an oligonucleotide according to claim 1, characterized in that a covalent link is produced by coupling a primary amine group of one strand and a carboxyl group of the other strand or of another portion of the same strand, by a condensation reaction at pH 6.5 in the presence of a condensing agent.

19. Method according to claim 18, characterized in that the condensing agent is water-soluble carbodiimide.

20. Method for preparing an oligonucleotide according to claim 18, characterized in that the strand containing a carboxyl group is prepared from a strand containing an amine group, obtained using a nucleotide synthon containing the hydroxyl groups of the 5' and 3' ends suitably protected in order for it to be used in a method of automatic or manual synthesis of nucleic acids and an amine group substituted at the 2' position protected by a trifluoroacetyl group, or using a non-nucleotide synthon, said amine group of which is deprotected and which is then coupled to an acid anhydride containing a said aliphatic group.

21. Method according to claim 20, characterized in that a nucleotide synthon is used in which said hydroxyl groups are protected by protective groups used in the phosphoramidite methods of oligonucleotide synthesis.

\* \* \* \* \*